United States Patent [19]

Grasselli et al.

[11] 4,424,141
[45] Jan. 3, 1984

[54] PROCESS FOR PRODUCING AN OXIDE COMPLEX CATALYST CONTAINING MOLYBDENUM AND ONE OF BISMUTH AND TELLURIUM

[75] Inventors: Robert K. Grasselli, Chagrin Falls; Dev D. Suresh, Macedonia; Maria S. Friedrich, Lyndhurst, all of Ohio

[73] Assignee: The Standard Oil Co., Cleveland, Ohio

[21] Appl. No.: 222,821

[22] Filed: Jan. 5, 1981

[51] Int. Cl.³ .................. B01J 21/02; B01J 23/18; B01J 23/28; B01J 27/18

[52] U.S. Cl. .................. 502/205; 260/465.3; 562/545; 562/547; 568/479; 568/480; 502/206; 502/207; 502/209; 502/211; 502/212; 502/215; 502/241; 502/242; 502/247; 502/248; 502/250; 502/255; 502/256; 502/257; 502/304; 502/306; 502/317; 502/320

[58] Field of Search ............... 252/435, 437, 439, 456, 252/458, 462, 465, 467, 469, 470, 432, 468; 260/465.3, 465 C, 346.75; 562/545, 546, 547; 568/476, 479, 480; 585/622, 624, 626

[56] References Cited

U.S. PATENT DOCUMENTS

| | | | |
|---|---|---|---|
| 3,238,254 | 1/1966 | Kerr | 260/530 |
| 3,637,526 | 1/1972 | Levy | 562/545 X |
| 3,959,182 | 5/1976 | Izawa et al. | 252/467 |
| 3,975,300 | 8/1976 | Burress | 252/435 |
| 4,003,978 | 1/1977 | Shiraishi et al. | 423/237 |
| 4,035,417 | 7/1977 | Ono et al. | 260/530 N |
| 4,147,661 | 4/1979 | Higgins et al. | 252/435 |
| 4,148,757 | 4/1979 | Brazdil et al. | 252/437 X |
| 4,212,766 | 7/1980 | Brazdil et al. | 252/437 X |
| 4,268,444 | 5/1981 | Franz et al. | 260/346.75 |
| 4,272,408 | 6/1981 | Daniel | 252/439 X |

Primary Examiner—Earl C. Thomas
Attorney, Agent, or Firm—J. E. Miller, Jr.; H. D. Knudsen; L. W. Evans

[57] ABSTRACT

Bismuth molybdate catalysts formed from a precatalyst slurry which uses an organic liquid or mixture of an organic liquid and water as the liquid medium of the slurry exhibit superior catalytic properties.

10 Claims, 2 Drawing Figures

PROCESS FOR PRODUCING AN OXIDE COMPLEX CATALYST CONTAINING MOLYBDENUM AND ONE OF BISMUTH AND TELLURIUM

BACKGROUND OF THE INVENTION

The present invention relates to catalysts useful in the oxidation and/or ammoxidation of olefins. More specifically, the present invention relates to a novel process for producing oxidation and/or ammoxidation catalysts having superior properties.

It is well known that olefins can be oxidized to oxygenated hydrocarbons such as unsaturated aldehydes and acids, for example, acrolein and methacrolein, and acrylic and methacrylic acids. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methocrolein and methacrylonitrile, isobutylene is the generally used olefin reactant.

Many different catalysts have been disclosed as useful in the oxidation and ammoxidation of olefins. For example, see U.S. Pat. Nos. 3,882,159 and 3,746,657. Also see commonly assigned application Ser. No. 748,609, filed Dec. 7, 1976, the disclosure of which is incorporated herein by reference. As will be noted, catalysts based on bismuth and molybdenum, i.e. bismuth molybdate catalysts, promoted with various additional elements such as iron, cobalt, nickel, potassium, phosphorus, chromium, manganese, cesium, antimony and the like shown special utility for these reactions.

Bismuth molybdate catalysts have been prepared in the past by a number of different techniques. For example, Example III of U.S. Pat. No. 3,746,657 shows a preparation method comprising forming a mixture of potassium hydroxide, ammonium molybdate and silica, adding to the mixture phosphoric acid, solutions in nitric acid of the nitrates of cobalt, iron, nickel and bismuth, and more silica to form a slurry, then spray drying and calcining to form the catalyst. Application Ser. No. 748,609 discloses a catalyst preparation technique in which an aqueous solution of cobalt nitrate and nickel nitrate, an aqueous solution of potassium nitrate and iron nitrate, and aqueous nitric acid solution of bismuth nitrate and a silica sol are added in order to an aqueous solution of ammonium heptamolybdate and phosphoric acid, and the composition so obtained spray dried and calcined to form the catalyst. That application discloses another catalyst preparation technique in which an aqueous nitric acid solution of ferric nitrate and bismuth nitrate is added to a previously formed aqueous slurry containing ammonium heptamolybdate, phosphoric acid, arsenic acid, silica sol, nickel nitrate and cobalt nitrate, the composition so obtained heated until a gel forms, and the gel dried and calcined to produce the ultimate catalyst. All of these techniques, it will be noted, have the common feature that the precatalyst slurry which is dried and then calcined to produce the ultimate catalyst is formed with water as the liquid medium of the slurry.

Each of the known techniques of catalyst preparation has relative advantages and disadvantages. Also, there has been some indication that the catalytic properties of the ultimate catalysts produced can be improved if specific catalysts preparation techniques are followed. As yet, however, there is no known catalyst preparation technique which is both simple and easy to perform and capable of enhancing the catalytic properties of the ultimate catalyst.

Accordingly, it is an object of the present invention to provide a catalyst preparation technique especially suited for preparing bismuth molydate type catalysts which is both simple and easy to perform as well as capable of enhancing the catalytic properties of the catalyst produced.

SUMMARY OF THE INVENTION

This and other objects are accomplished by the present invention in accordance with which a bismuth molybdate catalyst is prepared by a procedure in which the precatalyst slurry which is dried and calcined to produce the objective catalyst is formed using an organic liquid, or preferably a mixture of an organic liquid and water, as the liquid medium.

Thus, the present invention provides a novel process for producing a first stage oxide complex catalyst containing molybdenum and one of bismuth and tellurium in which a precatalyst precipitate or gel derived from a precatalyst slurry is calcined in an oxygen-containing gas to produce the catalyst, the improvement wherein the liquid medium of the slurry comprises methanol, ethanol, a non-alcoholic organic liquid or mixtures thereof.

DETAILED DESCRIPTION

Figure 1:
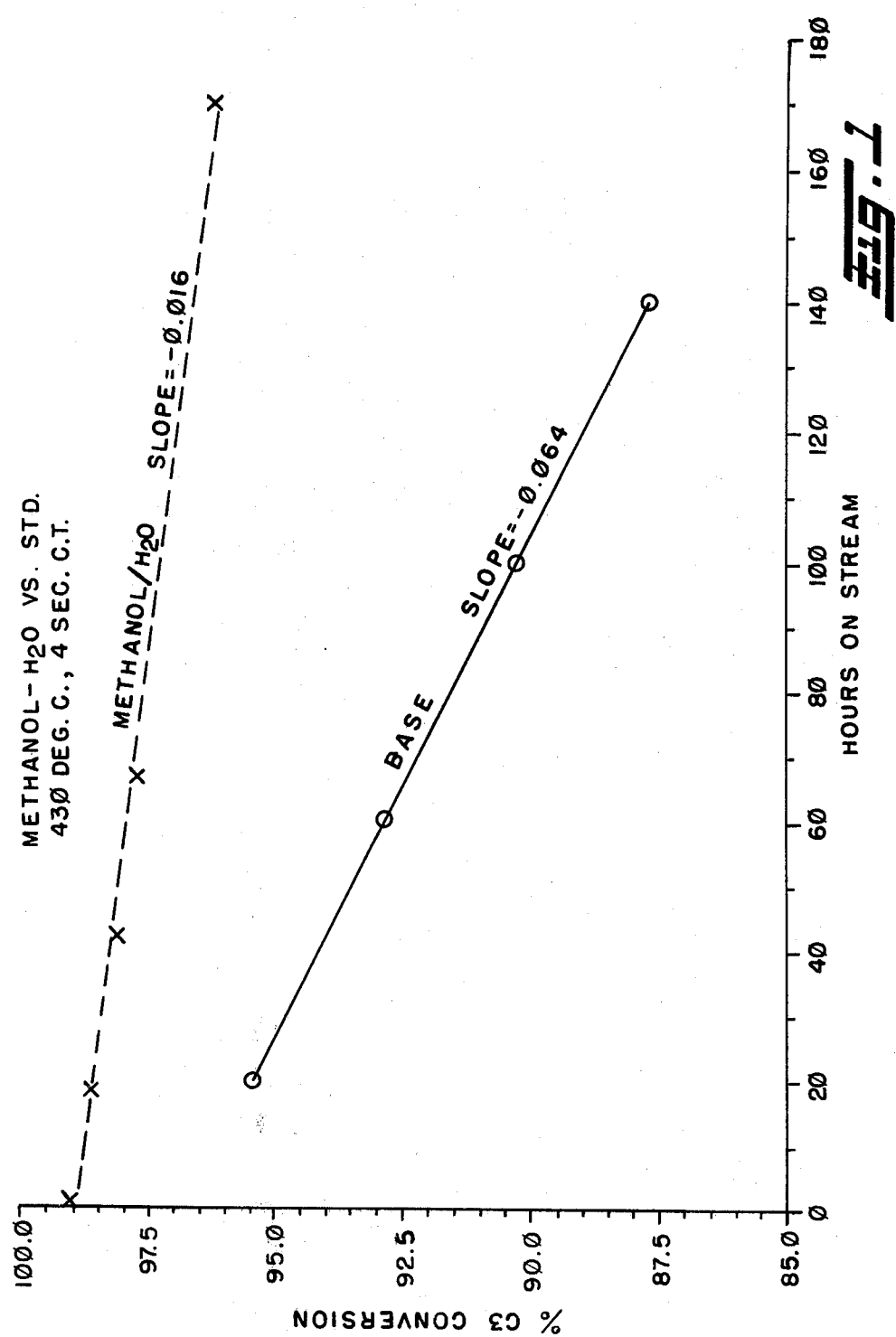
FIGS. 1 and 2 illustrate results obtained in the working examples.

The inventive catalyst preparation technique is applicable to certain molybdenum-containing catalysts which are known in the art as "first stage" catalysts. By "first stage" catalysts is meant that the catalysts show good activity in the conversion of propylene to acrolein but poor activity in the conversion of acrolein to acrylic acid. First stage catalysts are distinguished from "second stage" catalysts, which are catalysts showing poor activity in the conversion of propylene to acrolein but good activity in the conversion of acrolein to acrylic acid, and still other catalysts which are neither first stage catalysts nor second stage catalysts, e.g. maleic anhydride catalysts.

A wide variety of different oxide complex catalysts containing molybdenum and bismuth (or tellurium) are known in the art and described in many different patents, some of which are discussed above. A relative few of such patents indicate whether the catalysts disclosed are first stage catalysts, second stage catalysts or other type of catalysts. Furthermore, many patents disclose catalyst genuses including first and second stage catalysts, maleic anhydride catalysts, etc., without mentioning the differences between these catalysts. Nonetheless, the art recognizes that oxide catalysts containing both bismuth and molybdenum will exhibit good first stage activity, good second stage activity or neither.

Because of the complexity of oxide complex oxidation catalysts, there is no clear understanding in the art of exactly what features of a catalyst (e.g. composition, crystal structure, calcination history, etc.) make it function as a first stage, second stage or different type of catalyst. Certain observations, however, can be made. For example, second stage catalysts cannot normally be calcined for any length of time at temperatures above about 1,000° F. (537° C.), since they lose most if not all of their activity if treated in this way. On the other hand, first stage catalysts work best if calcined (final calcination) above 1,000° F., such as for example at 610° C. as shown in the working examples. In addition, it appears that first stage catalysts are "neutral" in character while second stage catalysts are "acidic" in character.

In this regard, certain elements in complex oxides can be regarded as acidic in nature in that they tend to form "metalate" anionic species. For example, molybdenum, tungsten and phosphorus readily form the molybdate, tungstate and phosphate anionic moieties which are acidic in nature. To a lesser extent, arsenic, vanadium, noibium, tantalum and antimony also exhibit an acidic nature. Other elements even in oxide form are basic in nature in that they act as cations. For example, the alkali metals are strongly cationic and hence strongly basic in character. In addition to the alkali metals, elements of Groups IB, II, III and VIII of the Periodic Table as well as manganese tend to function as basic cations. Still other elements are capable of exhibiting acid or basic characteristics depending on what other elements are present in the oxide complex.

Empirically it is possible to make a rough approximation of the acidic or basic character of an oxide complex by comparing the total positive valences of the cationic elements with the total negative valences of the metalate moieties derived from the anionic acting elements. Because some cationic elements such as iron may exist in more than one valence state and because of the amphoteric elements, this approximation cannot be too exact. In any event, using this type analysis it appears that most second stage catalysts have a significant excess of anionic species, i.e. are highly acidic, while most first stage catalysts have a reasonable balance of cationic and anionic ingredients and hence are relatively neutral. Analytically, however, it is extremely difficult or impossible to determine if such oxide complexes, which are oxides not acids or bases, exhibit an acidic or basic character. For this reason, the "neutral"/"acid" designations for first and second stage catalysts are still regarded as unconfirmed speculation. However, it is known that first and second stage catalysts are materially different from one another and from catalysts exhibiting neither first stage activity or second stage activity and that these differences can easily be determined by testing the catalyst in the first and second stage reactions as described above.

The catalyst to which the present invention applies are first stage catalysts, i.e. they are capable of catalyzing the conversion of propylene (and oxygen) to acrolein with acrolein yields of 50%, based on the propylene fed, but unable to catalyze the conversion of acrolein (plus oxygen) to acrylic acid in yeilds higher than 50%, based on the acrolein fed. The catalysts of the invention are further characterized as oxide complexes of the formula:

$$A_aG_bL_cD_dE_eMo_fO_x$$

wherein

A is an alkali metal, Tl, Cu, Ag and mixtures thereof, preferably K, Rb, Cs or mixtures thereof;

G is Ni, Co, Mn, Mg, a Group IIA element, Group IIB element or mixtures thereof, preferably Ni, Co, Mn, Mg, Zn, Cd or mixtures thereof, more preferably Ni and/or Co;

L is Fe, Cr, Ce, V and/or Eu, preferably Fe and optionally Cr;

D is Bi, Te or mixtures thereof, preferably Bi;

E is P, As, B, Sb, Ge, Sn, Si, Ti, Zr, rare earth and/or U or mixtures thereof;

Q is Mo and/or W, preferably Mo;

O is oxygen; and wherein a is 0–6, preferably 0.001–2;

b is 0–16, preferably 0.01–10;

c is 0–12, preferably 0.01–8;

d is 0.01–16, preferably 0.1–8;

e is 0–6, preferably 0–3;

f is 8–16, preferably 12; and x is determined by the valence state of the other elements.

Preferred catalysts of the above genus are those containing bismuth, iron and alkali metal. Of the preferred catalysts, more preferred are those containing potassium, rubidium and/or cesium as the alkali metal and at least one of cobalt and nickel. Catalysts which further contain chromium, antimony, manganese or mixtures thereof are especially preferred. In such catalysts, f is preferably 11 to 13.5, the chromium content if any is no more than 4, f is greater than a+b and the Bi/Mo ration is from 0.01/100 to 10/1, preferably 0.5/12 to 1/2 more preferably 0.7/12 to 2/12.

The catalysts of the invention may be used unsupported or supported on a support. Suitable support materials are $SiO_2$, $Al_2O_3$, $TiO_2$, $ZrO_2$, $SbPO_4$ and any other known conventional support material. The support material, for example $SiO_2$, can be added to the precatalyst slurry as a pure powder, e.g. silica powder such as Aerosil or Carbosil, or as a silica sol.

In accordance with the present invention, the precatalyst slurry or gel which is calcined to produce the catalyst product is derived from a precatalyst slurry which uses an organic liquid or a mixture of an organic liquid and water as the liquid slurry medium instead of all water as in conventional catalyst preparations.

As the organic liquid to be used in the inventive process, alcohols selected from methanol, ethanol, as well as any other non-alcohol organic solvent can be employed. Examples or appropriate non-alcohol organic solvents are glycols containing 1 to 10 carbon atoms, preferably 1 to 4 carbon atoms, crown ethers such as 18-crown-6, dimethylformamide, dimethylsulfoxide, ethanolamine, acetonitrile and the like. Preferred solvents are methanol, ethanol, ethylene glycol, 18-crown-6, dimethylformamide, dimethylsulfoxide, ethanolamine and acetonitrile. Especially preferred solvents are methanol and ethanol.

In the preferred embodiment of the invention, the liquid medium of the precatalyst slurry is composed of a mixture of an organic liquid and water. The amount of water in the liquid medium can vary widely but should be no more than 40 weight percent based on the total weight of the liquid in the slurry, excluding water of hydration. Preferably, the liquid medium contains 5% to 35% water, more preferably 10% to 30% water.

The amount of liquid medium to use in the precatalyst slurry as well as the procedures to be followed in forming the precatalyst slurry, drying the precatalyst slurry and calcining the dried precatalyst are all conventional. Of course, since many of the organic solvents employed are flammable, care should be taken during the processing of the precatalyst slurries to avoid combustion.

The compounds which are used to supply catalyst elements to the precatalyst slurry (hereinafter "source compounds") should be soluble in the slurry liquid into which they are introduced. For example, if the slurry medium is 100% ethanol, the catalyst elements making up the oxide complex should be introduced into the ethanol in the form of ethanol-soluble compounds such as for example acetates. If the slurry medium is a mixture of water and an organic liquid both water soluble and organic liquid soluble source compounds can be introduced into the organic liquid/water solution. In a particularly convenient way of practicing the invention as illustrated in some of the working examples, an aqueous component and an organic component are separately made with water soluble source compounds introduced into the aqueous component and organic liquid soluble source compounds introduced into the organic liquid. Thereafter the two components are combined to form the precatalyst slurry. In any event, it is desirable that source compounds be dissolved or substantially dissolved in the liquid into which they are introduced since this facilitates mixing of the catalyst elements as intimately as possible.

Incidentally, practically all catalysts of commercial interest will contain some support material and these materials as well are practically always insoluble in water as well as many organic liquids. These ingredients therefore do not normally dissolve in the slurry medium and indeed the presence of the materials is usually the reason why the precatalyst slurry is a slurry not a solution. This is entirely acceptable in accordance with the present invention. Also, it is known that elements of an oxide catalyst can be introduced into precatalyst slurries in the form of insoluble oxides. This is not preferred since such elements will not mix as intimately with the others as possible. However, it is possible to tolerate using insoluble oxides as source compounds as long as no more than 20 atom percent of the catalyst elements are supplied in this fashion.

As previously indicated, the precatalyst is processed in a conventional manner to yield the catalyst of the invention. Thus, the precatalyst slurry liquid is evaporated therefrom and the precatalyst precipitate obtained thereby calcined to decompose the source compounds and yield the catalyst of the invention. Calcination is accomplished in a conventional manner such as, for example, under the conditions disclosed in U.S. Pat. No. 3,642,930, the disclosure of which is incorporated herein by reference. As well known, care should be taken during such calcination to avoid heating the catalyst under such stringent conditions that the conventional crystalline bismuth molybdates are destroyed. Also, it is preferable to calcine at temperatures above about 540° C. (i.e. final calcination) since first stage catalysts are normally calcined at such higher temperatures. Indeed, another significant difference between first and second stage catalysts is that second stage catalysts are destroyed or seriously harmed if heated for any significant period of time over about 540° C., while first stage catalysts are conveniently calcined (final calcination) at temperatures significantly higher than 540° C. such as, for example, 610° C. as shown in the following examples.

As previously indicated, the catalysts of the present invention exhibit improved catalytic properties in the well known ammoxidation reaction in which propylene or isobutylene is reacted with ammonia and oxygen to produce acrylonitrile or methacrylonitrile, respectively. The improved catalysts produced by the inventive process can also be used in other oxidation-type processes such as the oxidation of propylene or isobutylene to produce acrolein and acrylic acid or methacrolein and methacrylic acid, respectively, as well as various oxydehydrogenation reactions such as the oxydehydrogenation of isoamylene to produce isoprene. Not only do the catalysts produced by the inventive process provide higher yields of useful products with higher selectivities in these reactions, but they can also in many instances be used at lower operating temperature and exhibit substantially improved catalyst stability and hence life characteristics.

WORKING EXAMPLES

The following working examples are provided to more thoroughly illustrate the present invention.

EXAMPLE 1

50% $K_{0.1}Ni_{2.5}Co_{4.5}Fe_3BiP_{0.5}Mo_{12}O_x$-50% $SiO_2$ 19.50 gms. silicomolybdic acid, 67.00 gms. NH$_4$ stabilized 40% silica sol and 1.16 gms. of a 42.5% aqueous solution of phosphoric acid were mixed together in about 100 cc. of ethanol to form Composition A. Separately, 12.12 gms. iron nitrate, 4.4 gms. bismuth triphenyl dissolved in hot ethanol, 13.10 gms. cobalt nitrate, 7.27 gms. nickel nitrate and 0.10 gms. potassium nitrate dissolved in a few drops of water were mixed together at room temperature in about 200 cc. of ethanol to form Composition B. Composition B had to be kept hot to prevent the bismuth from precipitating out. All of the nitrates except potassium nitrate dissolved in Composition B which formed a dark brown solution. Next, Composition B was added slowly to Composition A, and a brown precatalyst slurry resulted. The precatalyst slurry was heated with constant stirring until it began to solidify. The slurry was dried at 120° C. and then subjected to calcination by heating at 290° C. in air for 3 hours followed by heating at 425° C. for 3 yours. Final calcination was done at 610° C. for 3 hours.

EXAMPLE 2

A catalyst having a composition similar to that of Example 1 was prepared in the same way as the catalyst of Example 1, except that molybdenum was introduced onto Composition A in the form of ammonium heptamolybdate dissolved in water and all elements introduced into Composition B were in the form of acetates.

EXAMPLE 3

Example 2 was repeated except that solid silica (Aerosil) was used in place of the silica sol in order to avoid the water in the silica sol.

COMPARATIVE EXAMPLE A

Example 1 was repeated except that water was used in place of ethanol as the slurry medium, ammonium heptamolybdate was the molybdenum source and bismuth nitrate was the bismuth source.

COMPARATIVE EXAMPLE B

Example 2 was repeated except that the amount of catalyst produced was much larger than in Example 2, water was used in place of ethanol as the slurry medium, one of the elements in Composition B was introduced as an oxide and the other elements in Composition B were introduced as nitrates.

COMPARATIVE EXAMPLE C

Comparative Example B was repeated except that a small batch laboratory preparation the same size as Example 2 was conducted.

COMPARATIVE EXAMPLE D

Comparative Example A was repeated except that one-third of the iron and the phosphorus were added after Compositions A and B were combined.

EXAMPLE 4

The catalyst of Example 1 and Comparative Example A were charged into 5 cc. microreactors and contacted with a feed comprising 1.8 propylene/2.2 $NH_3$/3.6 $O_2$/2.4 $N_2$/6 $H_2O$ at 430° C. with a contact time of 6 seconds. After 1 hour onstream, the reaction products were recovered and analyzed. The results obtained are set forth in the following Table I.

TABLE I

| Ammoxidation of Propylene Feed: 1.8 $C_3=$ /2.2 $NH_3$/3.6 $O_2$/2.4 $N_2$/6 $H_2O$ | | | | | |
|---|---|---|---|---|---|
| | Time | | Mole % | | |
| Catalyst | Onstream (Hours) | Reaction Temp (C.) | Prop Conv | AN Yield | HCN Yield |
| Comp A | 1 | 430 | 98.7 | 75.7 | 4.6 |
| Ex 1 | 1 | 430 | 99.3 | 80.5 | 1.9 |

From the above Table I, it can be seen that catalysts produced by the inventive process provide acrylonitrile in significantly greater yields than a catalyst made by the conventional technique.

EXAMPLE 5

Example 4 was repeated using the catalyst of Example 2 and Comparative Catalyst B. The results obtained are set forth in the following Table II

TABLE II

| Ammoxidation of Propylene Feed: 1.8 $C_3=$ /2.2 $NH_3$/3.6 $O_2$/2.4 $N_2$/6 $H_2O$ | | | | | |
|---|---|---|---|---|---|
| Recovery | Time | | Mole % | | |
| Run and Catalyst | Onstream (Hours) | Reaction Temp (C.) | Prop Conv | AN Yield | HCN Yield |
| 1-Comp B | 18 | 430 | 94.8 | 76.0 | 5.5 |
| 2-Comp B | 1,000 | 430 | 95.8 | 72.7 | 7.7 |
| 3-Comp B | 1,000 | 445 | 97.7 | 74.4 | 7.3 |
| 1-Ex 2 | 18 | 430 | 98.4 | 79.9 | 2.2 |
| 2-Ex 2 | 1,000 | 430 | 99.0 | 77.9 | 6.4 |

As can be seen, acrylonitrile is produced in significantly greater yields when the catalysts of the present invention are employed.

EXAMPLE 6

Example 4 was repeated except that the catalysts of Example 3 and Comparative Example C were employed and the contact times were changed. The new contact times and the results obtained are set forth in the following Table III.

TABLE III

| Ammoxidation of Propylene Feed: 1.8 $C_3=$ /2.2 $NH_3$/3.6 $O_2$/2.4 $N_2$/6 $H_2O$ | | | | | | |
|---|---|---|---|---|---|---|
| | Time | | | Mole % | | |
| Catalyst | Onstream (Hours) | Reaction Temp (C.) | C.T. Sec | Prop Conv | AN Yield | HCN Yield |
| Comp C | 22 | 430 | 2.0 | 81.2 | 70.0 | 2.4 |
| Ex 3 | 21 | 430 | 1.7 | 99.6 | 77.1 | 5.1 |

From the above Table III, it can be seen that the catalyst produced by the inventive process provides acrylonitrile in significantly higher yields than the conventionally produced catalyst even though the contact time is shorter with the inventive catalyst.

EXAMPLE 7

The catalysts of Example 1 and Comparative Example D were employed in the oxidation of propylene to produce acrolein and acrylic acid. In these experiments, the catalysts were charged into 5 cc. microreactors and contacted with a feed comprising 1 propylene/8 air/4 $H_2O$ at 300° C. or 320° C. at 3 second contact times. The results obtained are set forth in the following Table IV.

TABLE IV

| Ammoxidation of Propylene Feed: 1 $C_3=$ /8 Air/4 $H_2O$ | | | | | |
|---|---|---|---|---|---|
| | | | Mole % | | |
| Recovery Run | Catalyst | Reaction Temp (C.) | Prop Conv | Acrol Yield | AA Yield |
| 1 | Comp D | 300 | 46.9 | 40.4 | 1.4 |
| 2 | Comp D | 320 | 71.9 | 65.5 | 2.3 |
| 1 | Ex. 1 | 300 | 87.2 | 74.5 | 5.3 |
| 2 | Ex. 1 | 320 | 96.2 | 83.1 | 5.9 |

From the above Table IV it can be seen that the catalysts produced by the inventive process provide acrolein and acrylic acid in much greater yields than the catalysts produced conventionally.

EXAMPLE 8

The catalysts of Examples 1 and Comparative Example D were also employed in the oxydehydrogenation of butene-1 to produce butadiene. In these experiments, a feed comprising 1 butene-1/11 air was contacted with 5 cc. of the indicated catalysts at 320° C. and 335° C. at a 1.5 second contact time. The results obtained are set forth in the following Table V.

TABLE V

| Oxydehydrogenation of Butene-1 Feed: 1 $C_4= -$ 1/11 Air | | | | |
|---|---|---|---|---|
| | | | Mole % | |
| Recovery Run | Catalyst | Reaction Temp (C.) | Propylene Conversion | Butadiene |
| 1 | Comp D | 320 | 32.2 | 30.2 |
| 2 | Comp D | 335 | 58.4 | 55.9 |
| 1 | Ex. 1 | 320 | 69.3 | 66.9 |
| 2 | Ex. 1 | 335 | 100.0 | 95.5 |

Again it can be seen that catalysts produced by the inventive process provide the desired end product in yields significantly greater than those obtained with conventionally prepared catalysts.

COMPARATIVE EXAMPLE E

Microreactor life tests were conducted on two separate batches of catalyst having the composition of and made in accordance with the procedure described in Comparative Example C.

2.5 cc. of the catalysts so obtained were mixed with 5 cc. of each of fused quartz and the whole mixture charged into microreactors. The catalysts were then heated to 430° C. and contacted with a feed comprising 1.8 propylene/2.2 NH$_3$/3.6 O$_2$/2.4 N$_2$/6 H$_2$O at a contact time of 4 seconds. These conditions are much more severe than normal and are used to accelerate activity declines which are inherent in such catalysts with use. The gross reaction product was periodically recovered and analyzed. The results are set forth in the following Table VI.

TABLE VI

Propylene Ammoxidation-Comparative Example E
Microreactor
Feed: 1.8 C$_3$ = /2.2 NH$_3$/3.6 O$_2$/2.4 N$_2$/6 H$_2$O

| Recovery Run | Cat Batch | Time On Stream (Hrs) | Norm Mole % Conv To | | | | Select | |
|---|---|---|---|---|---|---|---|---|
| | | | Unreac C3 | AN | HCN | AN+ HCN | AN | AN+ HCN |
| 1 | 1 | 1.0 | 3.4 | 79.0 | 2.0 | 81.0 | 81.8 | 83.8 |
| 2 | 1 | 26.5 | 6.4 | 78.7 | 2.4 | 81.1 | 84.0 | 86.6 |
| 3 | 1 | 51.0 | 8.1 | 77.6 | 2.7 | 80.3 | 84.4 | 87.4 |
| 4 | 1 | 71.0 | 8.1 | 77.9 | 2.9 | 80.8 | 84.8 | 87.9 |
| 1 | 1 | 1.5 | 3.2 | | | | | |
| 2 | 1 | 20.5 | 4.1 | 80.7 | 2.5 | 83.2 | 84.1 | 86.7 |
| 3 | 1 | 44.0 | 5.4 | | | | | |
| 4 | 1 | 68.0 | 7.4 | 78.2 | 3.0 | 81.2 | 84.4 | 87.7 |
| 5 | 1 | 142.0 | 11.8 | 73.2 | 4.3 | 77.5 | 83.0 | 87.9 |
| 1 | 2 | 1.0 | 2.5 | 81.6 | 2.2 | 83.8 | 83.7 | 85.9 |
| 2 | 2 | 24.0 | 4.7 | 79.2 | 3.1 | 82.3 | 83.1 | 86.4 |
| 3 | 2 | 50.5 | 7.3 | 77.6 | 3.6 | 81.2 | 83.7 | 87.6 |

EXAMPLE 9

Example 2 was repeated except that methanol was used as the slurry medium and bismuth was supplied as bismuth triphenyl. The catalyst so obtained was subjected to the same microreactor life tests as Comparative Example E. The results are set forth in the following Table VII.

TABLE VII

Propylene Ammoxidation-Example 9
Microreactor
Feed: 1.8 C$_3$ = /2.2 NH$_3$/3.6 O$_2$/2.4 N$_2$/6 H$_2$O
Rx. Temp.: 430° C.

| Recovery Run | Cat Batch | Time On Stream (Hrs) | Norm Mole % Conv To | | | | Select | |
|---|---|---|---|---|---|---|---|---|
| | | | Unreac C3 | AN | HCN | AN+ HCN | AN | AN+ HCN |
| 1 | | 1.0 | 1.0 | | | | | |
| 2 | | 18.0 | 1.4 | 82.2 | 3.5 | 85.7 | 83.4 | 86.9 |
| 3 | | 42.0 | 1.9 | 81.6 | 4.1 | 85.7 | 83.2 | 87.4 |
| 4 | | 66.0 | 2.3 | 80.8 | 4.3 | 85.1 | 82.7 | 87.1 |
| 5 | | 170.0 | 3.8 | 79.3 | 4.8 | 84.1 | 82.5 | 87.4 |

EXAMPLE 10

Example 9 was repeated four times except that the catalysts were made using ethanol rather than methanol as the alcohol. The catalysts were tested under the same conditions as Example 9 and the results are reported in the following Table VIII.

TABLE VIII

Propylene Ammoxidation-Example 10
Microreactor
Feed: 1.8 C$_3$ = /2.2 NH$_3$/3.6 O$_2$/2.4 N$_2$/6 H$_2$O
Rx. Temp.: 430° C.

| Recovery Run | Cat Batch | Time On Stream (Hrs) | Norm Mole % Conv To | | | | Select | |
|---|---|---|---|---|---|---|---|---|
| | | | Unreac C3 | AN | HCN | AN+ HCN | AN | AN+ HCN |
| 1 | 1 | 21.0 | 1.2 | 81.8 | 3.6 | 85.4 | 82.8 | 86.4 |
| 2 | 1 | 45.0 | 3.3 | 79.8 | 4.0 | 83.8 | 82.6 | 86.7 |
| 3 | 1 | 69.0 | 3.2 | 80.5 | 4.2 | 84.7 | 83.2 | 87.5 |
| 4 | 1 | 137.0 | 4.8 | 77.8 | 4.8 | 82.6 | 81.8 | 86.8 |
| 1 | 2 | 1.0 | 3.2 | 78.5 | 2.7 | 81.2 | 81.1 | 83.9 |
| 2 | 2 | 22.0 | 4.0 | 99.4 | 3.4 | 80.8 | 82.7 | 86.2 |
| 3 | 2 | 46.0 | 5.8 | 76.8 | 4.2 | 81.0 | 81.5 | 86.0 |
| 4 | 2 | 70.5 | 7.5 | 78.0 | 4.4 | 82.4 | 84.3 | 89.1 |
| 5 | 2 | 144.0 | 8.6 | 76.0 | 4.8 | 80.8 | 83.2 | 88.4 |
| 1 | 3 | 1.5 | 6.8 | 74.1 | 2.3 | 76.4 | 79.5 | 82.0 |
| 2 | 3 | 24.0 | 5.8 | 78.5 | 2.5 | 81.0 | 83.4 | 86.0 |
| 3 | 3 | 48.5 | 7.4 | 76.2 | 2.9 | 79.1 | 82.3 | 85.4 |
| 4 | 3 | 69.5 | 8.4 | 76.2 | 3.1 | 79.3 | 83.2 | 86.6 |

TABLE VIII-continued

Propylene Ammoxidation-Example 10
Microreactor.
Feed: 1.8 C3 = /2.2 NH3/3.6 O2/2.4 N2/6 H2O
Rx. Temp.: 430° C.

| Recovery Run | Cat Batch | Time On Stream (Hrs) | Norm Mole % Conv To | | | | Select | |
|---|---|---|---|---|---|---|---|---|
| | | | Unreac C3 | AN | HCN | AN+ HCN | AN | AN+ HCN |
| 5 | 3 | 138.5 | 12.2 | 73.4 | 4.2 | 77.6 | 83.5 | 88.4 |
| 1 | 4 | 21.5 | 1.7 | 78.2 | 3.2 | 81.4 | 79.6 | 82.8 |
| 2 | 4 | 45.0 | 2.1 | 79.4 | 4.0 | 83.3 | 81.1 | 85.1 |
| 3 | 4 | 69.5 | 1.9 | 79.1 | 4.4 | 83.4 | 80.6 | 85.0 |
| 4 | 4 | 141.8 | 3.5 | 77.4 | 5.0 | 82.4 | 80.2 | 85.4 |

Figure 2:
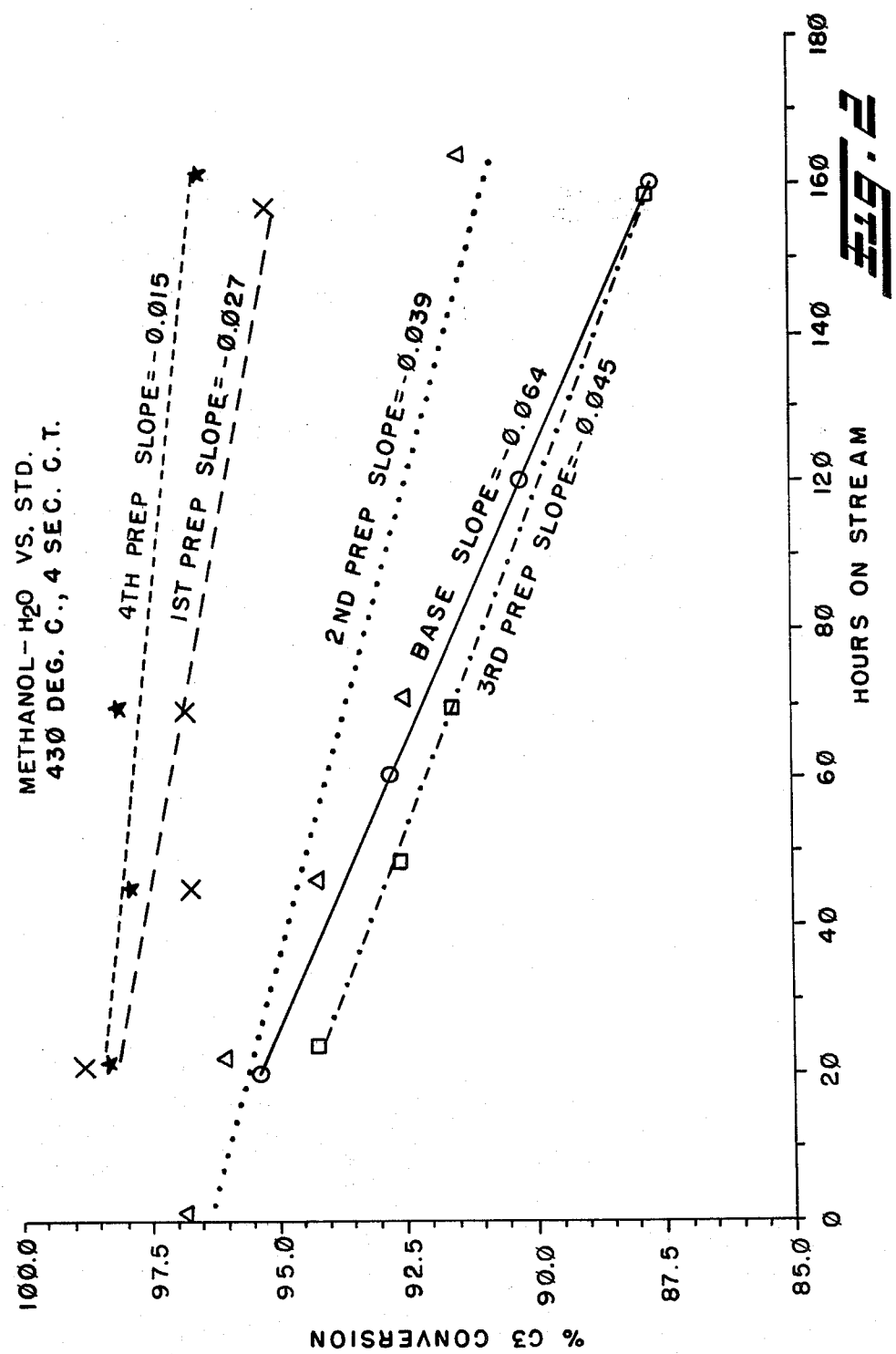

The above data show that catalysts produced by the invention are in general capable of producing acrylonitrile in higher yields than the conventionally prepared catalysts. Moreover, while acrylonitrile yields (conversion to acrylonitrile) of batches 2 and 3 of Example 10 were only about as good as those of Comparative Example E, FIGS. 1 and 2, which illustrate the decline in activity (total conversion) of the catalysts over time, show that catalysts of the invention lose their activity much more slowly than conventionally prepared catalysts. Specifically, FIGS. 1 and 2 show that the conventionally prepared catalyst (base case) under the comparatively severe reaction conditions of these examples exhibits a decline in activity of 0.064% propylene conversion per hour, while the activity declines for all the catalysts of the invention are significantly less, namely 0.016% for the catalyst of Example 9 and 0.027%, 0.039%, 0.045% and 0.015% for the four different catalysts of Example 10. Incidentally, the lines in FIGS. 1 and 2 representing the conventionally prepared catalyst are derived from a linear regression analysis of the three separate sets of runs of Comparative Example E.

Although only a few embodiments of the invention have been shown above, it should be appreciated that many modifications can be made without department from the spirit and scope of the invention. All such modifications are intended to be included within the scope of the invention, which is to be limited only by the following claims:

We claim:

1. In a process for producing a first stage oxide complex catalyst containing molybdenum and one of bismuth and tellurium in which a pre-catalyst precipitate or gel derived from a pre-catalyst slurry is calcined in an oxygen-containing gas to produce said catalyst, the improvement wherein the liquid medium of said slurry comprises methanol, ethanol or mixtures thereof, said oxide complex catalyst containing bismuth and having the formula

$$A_a G_b L_c D_d E_e Q_f O_x$$

wherein
  A is an alkali metal, Tl, Cu, Ag and mixtures thereof;
  G is Ni, Co, Mn, Mg, a Group IIA element, IIB element or mixtures thereof;
  L is Fe, Cr, Ce, V and/or Eu;
  D is Bi, Te or mixtures thereof;
  E is P, As, B, Sb, Ge, Sn, Si, Ti, Zr, rare earth and/or U or mixtures thereof;
  Q is Mo and/or W; and
wherein
  a is 0.001–2,
  b is 0.01–10,
  c is 0.01–8,
  d is 0.1–8,
  e is 0–3, and
  f is 11–13.5.
  x is determined by the valence state of the other elements present.

2. The process of claim 1 wherein
  A is K, Rb, Cs or mixtures thereof,
  G is Ni, Co, Mn, Mg, Zn, Cd or mixtures thereof,
  L is Fe and optionally Cr; and
  D is Bi and Q is Mo.

3. The process of claim 2 wherein said catalyst contains at least one of Cr, Sb and Mn.

4. The process of claim 3 wherein f is greater than a+b and the Bi/Mo ratio is 0.5/12 to ½.

5. The process of claim 4 wherein said liquid medium contains 5 to 35% water.

6. The process of claim 5 wherein said liquid medium contains 10 to 30% water.

7. The process of claim 2 wherein f is greater than a+b and the Bi/Mo ratio is 0.5/12 to ½.

8. The process of claim 7 wherein said liquid medium contains 5 to 35% water.

9. The process of claim 8 wherein said liquid medium contains 10 to 30% water.

10. The process of claim 2 wherein said liquid medium contains water in an amount of up to 40 weight-percent.

* * * * *